Sept. 15, 1936. V. S. HILLOCK Plant Pat. 194
ROSE
Filed Dec. 12, 1935
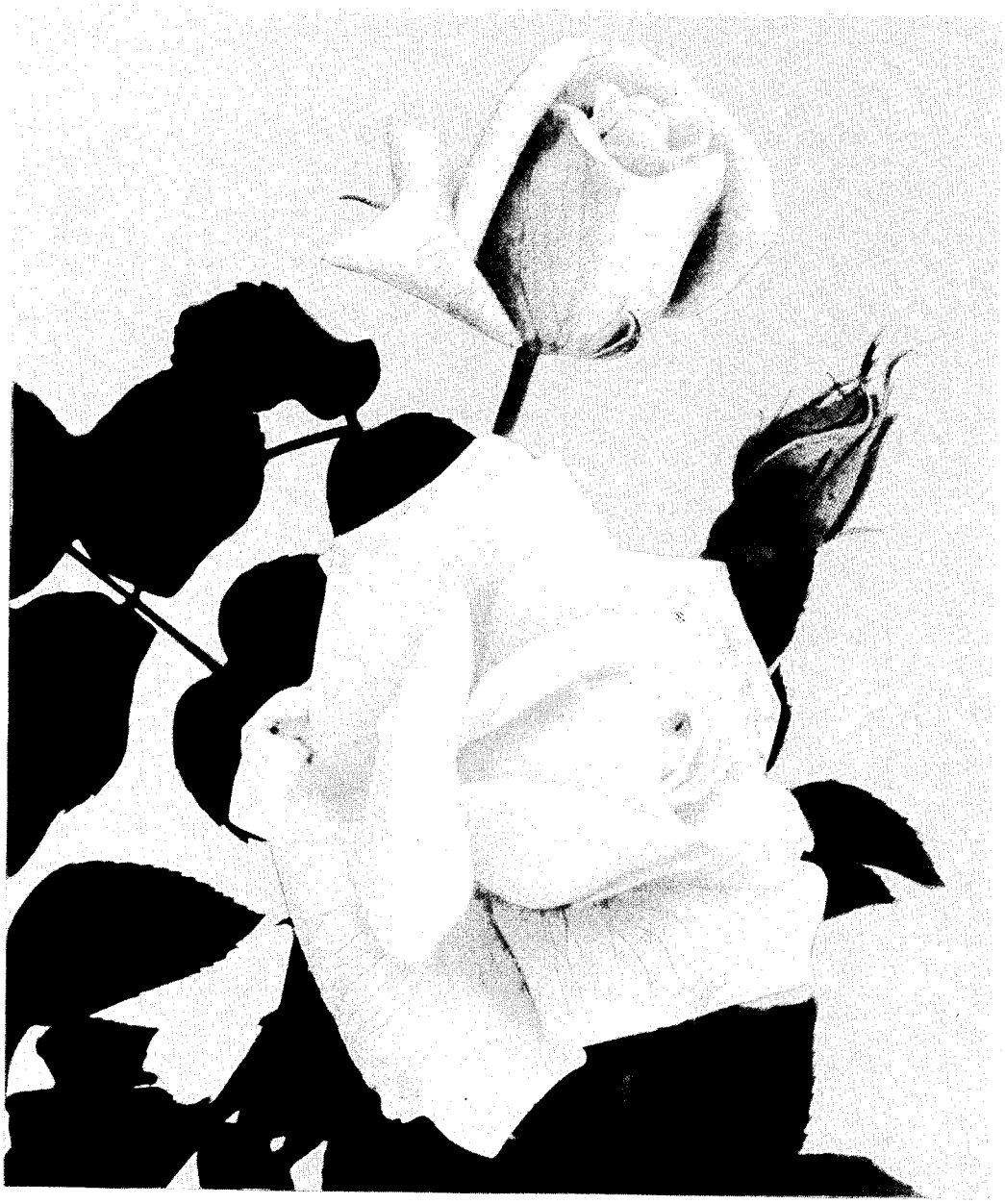
INVENTOR
Verne Stone Hillock
By Orville M. Kile
PLANT PATENT AGENT Patented Sept. 15, 1936

UNITED STATES PATENT OFFICE

194

ROSE

Verne Stone Hillock, Arlington, Tex.

Application December 12, 1935, Serial No. 54,126

1 Claim. (Cl. 47—61)

My present invention relates to improvements in hybrid-pernetiana roses. The object of this invention is to provide a new and distinct variety of rose of the type mentioned, having desirable and pleasing color qualities as well as other desirable characters which will hereinafter appear.

This new variety of rose was produced by crossing the variety Etoile de Feu (pollen parent) and an unnamed seedling, by the usual cross-breeding methods. This variety has been reproduced extensively from cuttings to prove its fixity of qualities and has been tested in a number of widely separated States. It has not yet been placed in commerce or offered to the public.

The accompanying illustration shows in full color and with approximate accuracy, a tight bud, a partly opened flower, and a flower in its prime, as well as foliage of this new variety. It must be understood, however, that there will be considerable variations in color of flowers at different seasons and when grown under different conditions of soil and climate.

*The flower*

The following description is based on observations made by myself at Arlington, Texas, over a period of years. Except where otherwise noted, these observations relate to buds and blossoms of the first burst of bloom in the springtime.

*Blooming habit.*—Continuous bloomer throughout the season except during August.

Buds:

*Size.*—Medium.

*Form.*—Ovoid. (The bud is ovoid in such slight degree that it becomes pointed upon the first slight movement of the petals in opening.)

*Weather effects.*—Not affected in appreciable degree by either wet or hot weather.

*Color.*—Same as bloom, except that the tight bud is notably a deeper pink.

*Sepals.*—The sepals are very finely serrated and are branched. The branches are also serrated. The sepals extend above the bud, forming a hood, which is rather long. The sepals do not turn back before the outer petals are ready to unfurl. The sepals are permanent.

*Calyx.*—The calyx is conical, slightly hairy, and gives off a resinous odor when rubbed.

*Peduncle.*—The peduncle is long; moderately prickly; sometimes green, sometimes bronzy-green; moderately strong (usually holding flower upright).

*Opening.*—The bud opens well in all weathers.

Bloom:

*Size.*—Medium. Three and one-half to four and one-half inches.

*Borne.*—Singly and in sprays (several together). When borne in sprays, one large center blossom opens first and passes. Then the remaining buds open simultaneously.

*Stems.*—Some long to very long; some medium length. The former are strong to very strong; the latter medium.

*Form.*—The blossom is usually cupped, retaining such form to the end. However, an occasional blossom appears upon which the petals quill, as with a cactus dahlia.

*Petalage.*—Under normal conditions the number of petals varies from thirty to forty-five.

*Color.*—The rose is classed as an orange-pink, the color varying throughout the season. In early spring the color is orange with a strong pink underglow. In heat it becomes a brilliant pink with a strong orange suffusion, the resulting color approaching Flame Scarlet in Plate II of Ridgway's Color Standards and Nomenclature, although it has slightly more of an admixture of cerise or scarlet in it than is shown in this color plate. Under the effects of cool night temperatures in autumn the pink color deepens to prawn-red, with a strong orange suffusion, the resulting color approaching Scarlet-Red in Plate I of Ridgway's Color Standards although not quite so dark and a little more of the cerise hue. In each instance the color is uniform throughout the flower, with the exception of a base of gold and deep salmon markings on the reverse of the outer petals.

Petals:

*Appearance.*—Inside shiny; outside shiny.

*Texture.*—Moderately thin; moderately soft. Not affected by wet weather. Will burn only in extreme heat.

*Forms.*—Usually oval with slight scallops at edge. An occasional blossom carries narrower petals—these petals quill.

*Arrangement.*—Imbricated. Often three or four petaloids at center.

*Persistence.*—Petals drop off cleanly.

*Fragrance.*—Moderate. Fruity.

*Longevity.*—On plant—fair. As cut flower—fair.

Genital organs:

*Stamens.*—The medium sized anthers are yellow. The medium lengthed filaments are pinkish-yellow. Very numerous.

*Pollen.*—Golden yellow.

*Styles.*—Bunched; medium length; wavy; mostly of even length.

*Stigmas.*—Inside yellow; outside lightly banded with pink near terminus, the pink extending in streaks down styles of varying lengths.

*Ovaries.*—They are habitually tightly enclosed.

Fruit:

This variey is fertile with its own pollen, bearing fruit in moderation.

*Form.*—Urn shaped, with flat head.

*Aspect.*—Smooth.

*Color at maturity.*—Brownish-yellow.

*Sepals.*—The sepals are permanent, usually standing straight.

*The plant*

Form:

Bush.

Growth:

Vigorous; upright. The plant breaks freely both from the base and from high in the plant.

Foliage:

*Leaflets.*—Usually five, sometimes seven.

*Size.*—Medium.

*Quantity.*—Normal.

*Color.*—New foliage, bronzy-green; old foliage, normal green.

*Shape.*—Pointed.

*Texture.*—Upper side, leathery and smooth; lower side, smooth except for ribs and veins. Medium heavy.

*Edge.*—Serrated.

*Serrations.*—Single.

*Leaf stem.*—Green. Narrow. No prickles, except in rare instances.

*Disease resistance.*—Resistant to black spot and mildew.

Wood:

New wood, normal green with bronze shadings. Old wood, green but slightly lighter than the new wood, as though it had been given a slight gold suffusion.

Thorns:

*Quantity.*—Ordinary for a hybrid-Pernetiana.

*Form.*—Narrow base; hooked slightly downward.

*Color when young.*—Red. Color when old: Dark brown.

*Position.*—Irregular.

*Prickles.*—None on canes or stems.

*Short needles.*—None on canes or stems.

This is the first known variety of the approximate color described and shown, that develops a hard-wooded, vigorous and productive plant or bush.

*Comparisons*

The known varieties which most nearly resemble this new variety are Mari Dot and Rosella Sweet, although there are distinct differences.

Of the three varieties this new variety is the fullest rose, carrying twice as many petals as Mari Dot and being fuller than Rosella Sweet by the ratio of five to three. Neither Mari Dot nor Rosella Sweet ever produces blossoms with quilled petals but this new variety frequently produces such blossoms.

The color of Rosella Sweet differs from the color of this new variety in the direction of orange; the color of Mari Dot differs in the direction of cerise—in both the spring and fall blossoms. In both instances the difference is minor but plainly apparent.

This new variety differs markedly from Mari Dot in that the bush of the latter grows into an extremely awkward form with branches in horizontal position and its foliage is highly susceptible to disease, making it difficult to keep alive under average conditions; while the bush of this new variety grows upright and vigorously and the foliage is disease resistant in such degree as to give real vigor.

This new variety differs from Rosella Sweet and Mari Dot, in part, in that the bush of the latter two is very soft-wooded and the foliage fleeting, as contrasted with the hard wood and disease resistant foliage of this new variety. The wood of this new variety remains distinctly green when frosted, as contrasted with Rosella Sweet and Mari Dot and other hybrid tea roses, most of which show strong color changes when the wood is frosted.

Having thus disclosed my invention, I claim:

The variey of hybrid-Pernetiana rose plant shown and described, characterized particularly by its hard wooded development and disease resistant foliage and its flowers of distinctive orange-pink color.

VERNE STONE HILLOCK.